United States Patent
Tannhauser et al.

[11] Patent Number: 6,016,682
[45] Date of Patent: Jan. 25, 2000

[54] SWAGING APPARATUS FOR SURGICAL NEEDLES

[75] Inventors: Robert J. Tannhauser, Bridgewater, N.J.; Martin T. Zdanowicz, Washington Crossing, Pa.; Himanshu Patel, San Jose, Calif.; Richard L. Dalrymple, Jr., Phillipsburg, N.J.

[73] Assignee: Ethicon, Inc., Somerville, N.J.

[21] Appl. No.: 09/131,983

[22] Filed: Aug. 11, 1998

[51] Int. Cl.⁷ .................................................. B21D 41/04
[52] U.S. Cl. ................................. 72/397; 72/402; 163/1; 29/243.517
[58] Field of Search .............................. 72/397, 396, 400, 72/402; 163/1, 5; 29/243.519, 243.517

[56] References Cited

U.S. PATENT DOCUMENTS

| | | | |
|---|---|---|---|
| 3,619,885 | 11/1971 | Dischler . | |
| 3,695,087 | 10/1972 | Tuberman | 72/402 |
| 3,924,440 | 12/1975 | Vinje | 72/397 |
| 4,041,766 | 8/1977 | Johnson et al. . | |
| 4,308,744 | 1/1982 | Baker | 72/402 |
| 4,567,650 | 2/1986 | Balyasny et al. | 29/283.5 |
| 4,614,107 | 9/1986 | Norin | 72/402 |
| 4,660,403 | 4/1987 | Slasinski | 72/389 |
| 5,051,107 | 9/1991 | Korthoff | 606/224 |
| 5,230,352 | 7/1993 | Putnam et al. | 163/1 |
| 5,350,373 | 9/1994 | Colligan | 72/402 |
| 5,394,971 | 3/1995 | Colligan et al. . | |
| 5,411,521 | 5/1995 | Putnam et al. | 72/402 |
| 5,462,543 | 10/1995 | Colligan | 72/402 |
| 5,608,962 | 3/1997 | Colligan et al. | 163/1 |
| 5,644,944 | 7/1997 | Dischler | 72/400 |

FOREIGN PATENT DOCUMENTS

| | | | |
|---|---|---|---|
| 1392175 | 2/1965 | France | 72/402 |
| 8238251 | 9/1996 | Japan . | |
| 1156858 | 3/1999 | Japan . | |
| 727305 | 4/1980 | Russian Federation . | |
| 867503 | 9/1981 | Russian Federation . | |
| 940996 | 7/1982 | Russian Federation | 72/402 |
| 1003988 | 3/1983 | Russian Federation | 72/402 |
| 1426689 | 9/1983 | Russian Federation . | |
| 617154 | 7/1978 | U.S.S.R. | 72/402 |

*Primary Examiner*—Daniel C. Crane
*Attorney, Agent, or Firm*—Selitto & Associates, P.C.

[57] ABSTRACT

A swaging apparatus for attaching sutures to surgical needles includes at least a first die and a second die. The first die has a first member, which includes a first surface, and a second member, which includes a second surface. The second member is movable relative to the first member between an extended position, in which the second surface extends beyond the first surface, and a retracted position, in which the second surface does not extend beyond the first surface. The second die has at least one surface and is movable relative to the first die between a remote position and an adjacent position. When the second die moves relative to the first die from the remote position towards the adjacent position, the second member of the first die is caused to move from the extended position towards the retracted position, and the surfaces of the first and second dies cooperate with one another so as to swage a surgical needle positioned between the first and second dies. The second member of the first die is movable to the retracted position when the second die abuts the first die. In this manner, surgical needles of many different types or sizes can be swaged by the swaging apparatus.

23 Claims, 9 Drawing Sheets

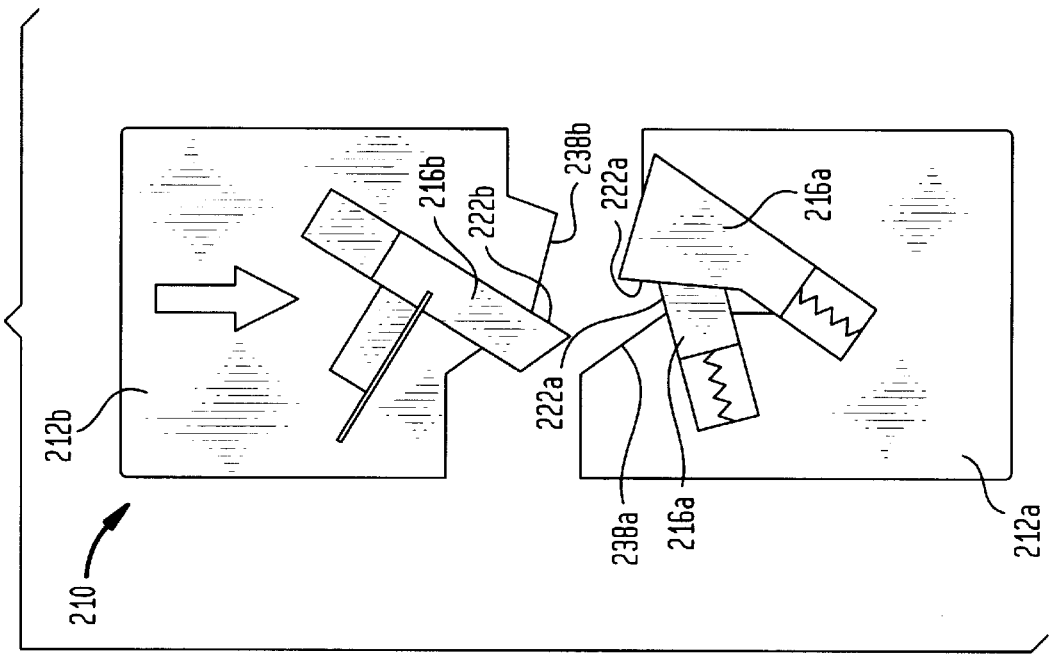
FIG. 13
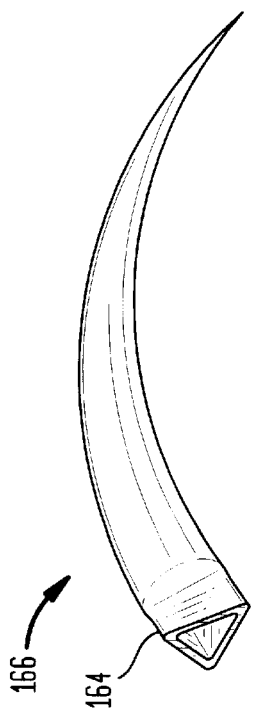
FIG. 12
FIG. 14

SWAGING APPARATUS FOR SURGICAL NEEDLES

FIELD OF THE INVENTION

The present invention relates to swaging apparatus, and, more particularly, to swaging apparatus adapted for use in attaching surgical sutures to surgical needles.

BACKGROUND OF THE INVENTION

A conventional swaging device for attaching a suture to a surgical needle typically has a pair of dies (see, for instance, U.S. Pat. Nos. 5,350,373, 5,394,971, 5,462,543 and 5,608, 962). In operation, the dies are pressed against each other so as to compress (i.e., swage) a mounting end of an associated surgical needle and suture placed therebetween, thereby attaching the suture to the needle.

The dies of this type of swaging device have a predetermined size and shape specifically corresponding to a preselected size and/or type of surgical needles, as well as a preselected size and/or type of surgical sutures. Surgical needles are available in many varying sizes (e.g., different outer diameters and suture hole sizes) and types (e.g., mechanically drilled needles, laser-drilled needles, punched-channel needles, open-channel needles and pre-closed-channel needles). Surgical sutures are also available in many different sizes and types (e.g., monofilament sutures and braided sutures). As a result, this type of swaging device requires numerous sets of dies for many different sizes and types of needles and/or sutures. Accordingly, in order to swage a needle having a different size, a previously mounted die set typically needs to be removed from an associated press and replaced with a die set which corresponds to the new needle size, thereby rendering the operation of the swaging device inefficient.

Japanese Pat. Publication No. 8238251 A discloses a swaging device having a pair of opposing swage blocks. Each of the blocks includes a swage surface and a projecting portion extending from the swage surface in dimension less than that of an associated needle. One of the blocks is movable, while the other one is stationary. In operation, the movable block moves towards the stationary block in a direction perpendicular to the swage surfaces until the projecting portions come in contact with the swage surfaces of the opposing blocks, thereby partially swaging the needle positioned between the blocks. The movable block is then moved in another direction and thereby completes the swaging operation. Because this swaging device performs a swaging operation in two separate steps, its operation is inefficient.

Other types of swaging devices are known (see, for instances, Russian Patent Publication Nos. 727305, 867503, 940996, 1003988 and 1426689). It is, however, believed that these devices are not adapted for efficient and universal use in connection with various types and sizes of surgical needles and/or sutures.

SUMMARY OF THE INVENTION

The present invention overcomes the disadvantages and shortcomings of the prior art discussed above by providing a new and improved swaging apparatus adapted for efficient and universal use in connection with surgical needles and sutures of many different types and sizes. More particularly, the swaging apparatus is provided with a first die having a first member, which includes a first surface, and a second member, which includes a second surface. The second member is movable relative to the first member between an extended position, in which the second surface projects beyond the first surface, and a retracted position, in which the second surface does not project beyond the first surface. The apparatus is also provided with at least one other die having at least one surface. The other die also causes the second member of the first die to move from the extended position towards the retracted position when the other die moves relative to the first die from a first position, in which it is remote from the first die, towards a second position, in which it is adjacent the first die. The surface of the other die cooperates with the first and second surfaces of the first die so as to swage a surgical needle positioned between the first die and the other die when the other die moves relative to the first die from the first position towards the second position. The second member of the first die is movable to the retracted position when the other die abuts the first die, whereby surgical needles of many different types or sizes can be swaged by the first die and the other die.

BRIEF DESCRIPTION OF THE DRAWINGS

For a more complete understanding of the present invention, reference is made to the following detailed description of various exemplary embodiments considered in conjunction with the accompanying drawings in which:

FIG. 12 is a view of a needle swaged by the swaging apparatus shown in FIG. 11;

FIG. 13 is a schematic view of a swaging apparatus constructed in accordance with a third embodiment of the present invention;

FIG. 14 is a view of a surgical needle swaged by the apparatus shown in FIG. 13;

DETAILED DESCRIPTION OF THE EXEMPLARY EMBODIMENTS

Figure 1:
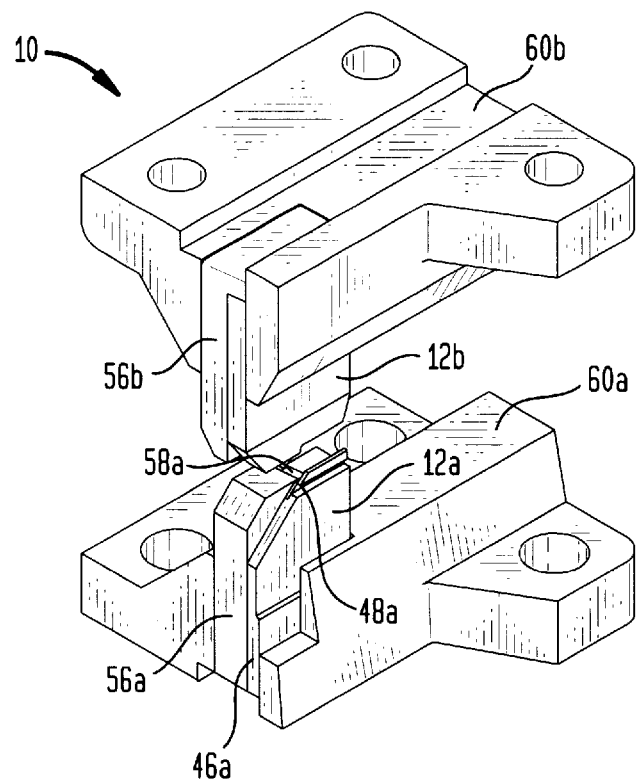
FIG. 1 is a perspective view of a swaging apparatus constructed in accordance with a first embodiment of the present invention.
Figure 2:
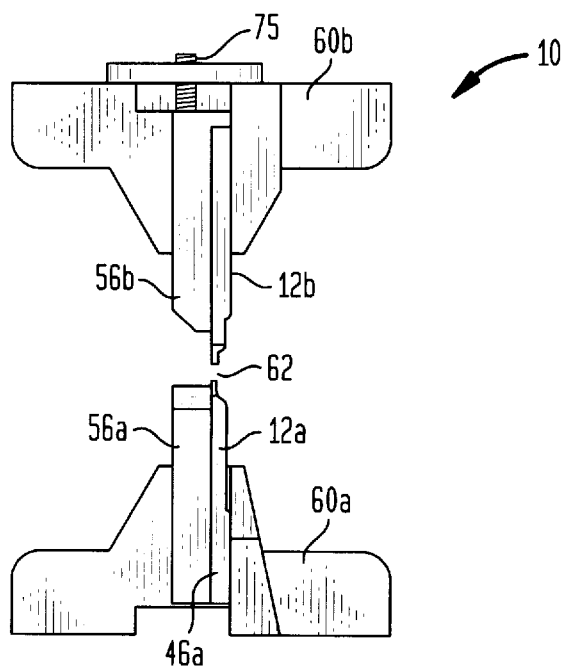
FIG. 2 is a front elevational view of the swaging apparatus shown in FIG. 1.
Figure 3:
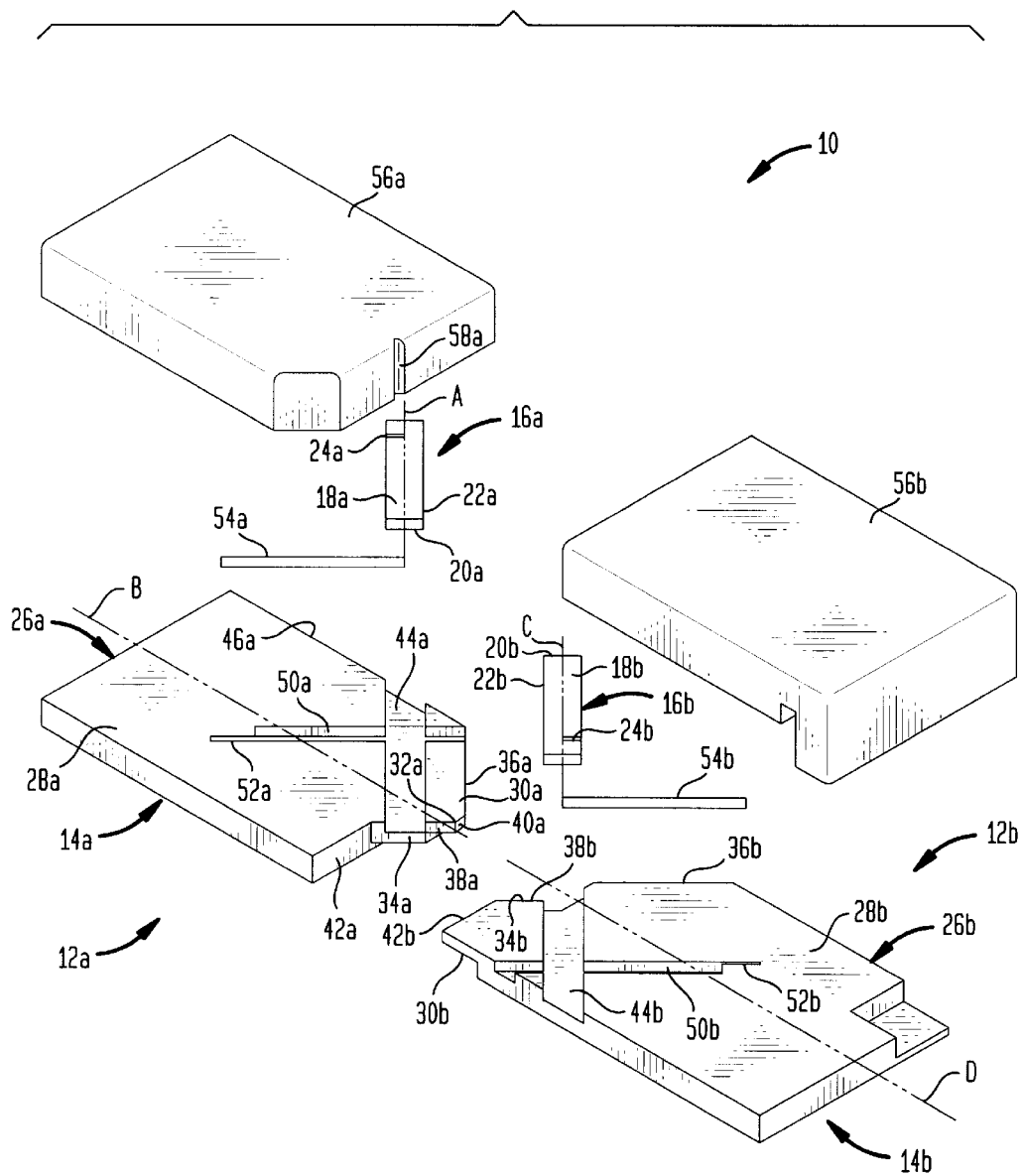
FIG. 3 is an exploded perspective view of a pair of swaging dies which are utilized in the swaging apparatus shown in FIGS. 1 and 2.
Figure 4:
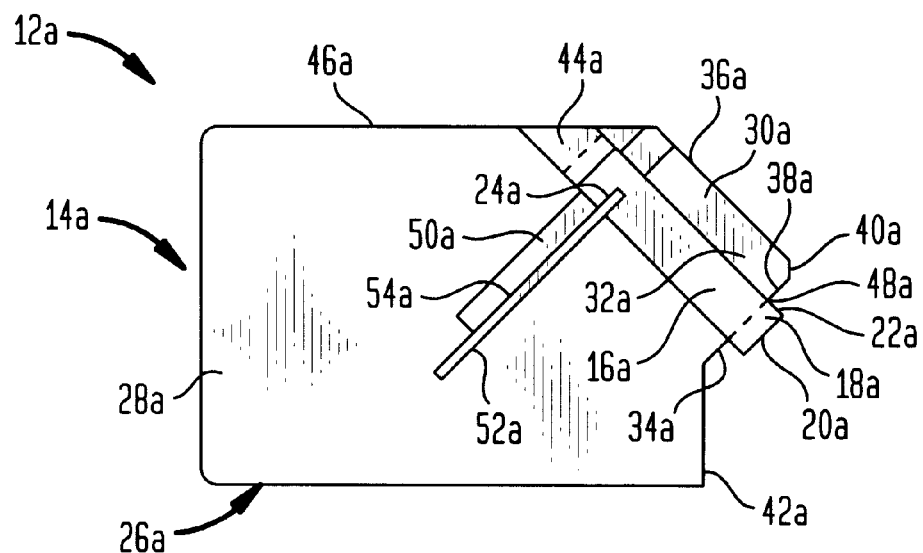
FIG. 4 is a top plane view of one of the dies shown in FIG. 3.

FIGS. 1 and 2 show a swaging apparatus 10 having a pair of swaging dies 12a, 12b. Referring to FIGS. 3 and 4, the die 12a is provided with a base die member 14a and a sliding die member 16a movably mounted in the base die member 14a. More particularly, the sliding die member 16a, which is provided with a thin, elongated box-like shape, includes a swaging portion 18a at one end thereof. The swaging portion 18a has an engaging surface 20a which lies in a plane substantially normal to a longitudinal axis A (see FIG. 3) of the sliding die member 16a. A contact surface 22a is formed in the swaging portion 18a. The contact surface 22a is substantially normal to the engaging surface 20a (i.e., the contact surfaces 22a lies in a plane which is substantially normal to the plane associated with the engaging surface 20a). A slit 24a is formed at an opposite end of the sliding die member 16a for a purpose to be discussed hereinafter. The swaging portion 18a of the sliding die member 16a has a thickness (i.e., the distance measured in a direction substantially parallel to both of the planes associated with the engaging and contact surfaces 20a, 22a) representing a land width for a surgical needle to be swaged (i.e., the longitudinal length of a swaged section of the needle).

Still referring to FIGS. 3 and 4, the base die member 14a includes a body 26a having a surface 28a which lies in a plane substantially parallel to a longitudinal axis B of the body 26a. The body 26a also includes a projection 30a located at one end of the body 26a and having a tip portion 32a and a pair of sides 34a, 36a. The side 34a is oriented substantially at a 45° angle with respect to the longitudinal axis B of the body 26a. Likewise, the side 36a of the projection 30a is inclined at an acute angle relative to the longitudinal axis B of the body 26a for purposes to be discussed hereinafter. The tip portion 32a includes a contact surface 38a formed in the side 34a of the projection 30a. Because the contact surface 38a is formed in the side 34a, it lies in a plane which is oriented at a similar acute angle (e.g., a 45° angle) relative to the longitudinal axis B of the 20 body 26a and which is substantially normal to the plane associated with the surface 28a of the body 26a. The tip portion 32a also has a flattened end surface 40a which lies in a plane substantially normal to the longitudinal axis B of the body 26a. The tip portion 32a has a uniform thickness (i.e., the distance measured along a direction substantially normal to the surface 28a of the body 26a) which is substantially identical to that of the swaging portion 18a of the sliding die member 16a. Accordingly, the contact surface 38a has a height (i.e., a land width) substantially identical to that of the contact surface 22a of the sliding die member 16a. A shoulder 42a is also provided on the body 26a for purposes to be discussed hereinafter.

The body 26a also includes a groove 44a formed in the surface 28a of the body 26a (see FIGS. 3 and 4). The groove 44a extends from the side 34a of the projection 30a to a side 46a of the body 26a along a direction substantially normal to the contact surface 38a of the projection 30a (i.e., normal to the plane associated with the contact surface 38a). The groove 44a is sized and shaped so as to movably receive the sliding die member 16a therein. More particularly, the sliding die member 16a is placed in the groove 44a in such a manner that the contact surface 22a of the sliding die member 16a is substantially normal to the contact surface 38a of the projection 30a (i.e., the plane associated with the contact surface 22a is substantially normal to the plane associated with the contact surface 38a). The groove 44a is also sized and shaped in such a manner that the sliding die member 16a is movable along a direction substantially normal to the plane associated with the contact surface 38a of the projection 30a between a fully extended position (as indicated by the solid line representation of the sliding die member 16a in FIG. 4) and a fully retracted position (as indicated by the broken line representation of the sliding die member 16a in FIG. 4). In the extended position of the sliding die member 16a, the swaging portion 18a projects outwardly from the groove 44a in dimension greater than an outer diameter of a surgical needle to be swaged. More particularly, the contact surface 22a of the sliding die member 16a extends outwardly from (i.e., beyond) the contact surface 38a of the projection 30a substantially at a 90° angle and thereby cooperates with same to form a V-shaped space 48a (see FIG. 4). In the retracted position of the sliding die member 16a, the swaging portion 18a is completely retracted into the groove 44a. In other words, the engaging surface 20a of the sliding die member 16a is substantially flush (i.e., coplanar) with the contact surface 38a of the projection 30a (i.e., the contact surface 22a of the sliding die member 16a does not extend beyond the contact surface 38a of the projection 30a). The groove 44a also has a depth (measured in a direction substantially normal to the surface 28a of the body 26a) such that the contact surface 22a of the sliding die member 16a is substantially aligned with the contact surface 38a of the projection 30a (i.e., the contact surface 22a and the contact surface 38a are positioned at the same level) and that the sliding die member 16a does not protrude above the groove 44a.

Still referring to FIGS. 3 and 4, the body 26a has a channel 50a and a slot 52a formed in the surface 28a. More particularly, the channel 50a intersects the groove 44a, while the slot 52a extends from an end of the channel 50a away from the groove 44a. The body 26a is also provided with a leaf spring 54a positioned in the channel 50a for causing the sliding die member 16a to normally assume its extended position. The leaf spring 54a has one end inserted in the slot 52a of the body 26a and an opposite end inserted in the slit 24a of the sliding die member 16a. The channel 50a is sized and shaped so as to allow the leaf spring 54a to resiliently bend in response to the movement of the sliding die member 16a. When the sliding die member 16a moves towards its retracted position, the leaf spring 54a urges the sliding die member 16a towards the extended position.

With reference to FIGS. 1–3, the die 12a is also provided with a holding plate 56a which includes a V-shaped notch 58a (see FIGS. 1 and 3) formed in one side of the holding plate 56a. More particularly, the holding plate 56a is applied to the surface 28a of the body 26a of the base die member 14a in such a manner that the notch 58a of the holding plate 56a is substantially aligned with the V-shaped space 48a formed by the contact surfaces 22a, 38a of the die 12a (see FIG. 1). Alternatively, the notch 58a can be formed in a member adjustably mounted to the holding plate 56a such that its position can be adjusted relative to the holding plate 56a and/or the base die member 14a. The holding plate 56a is adapted to contain the sliding die member 16a and the leaf spring 54a in the groove 44a and the channel 50a, respectively, during operation. The holding plate 56a and the die 12a are held in proper position relative to one another by a stationary die holder 60a (see FIGS. 1 and 2) which is immovably mounted to a conventional press (not shown) for operating the swaging apparatus 10.

Figure 5:
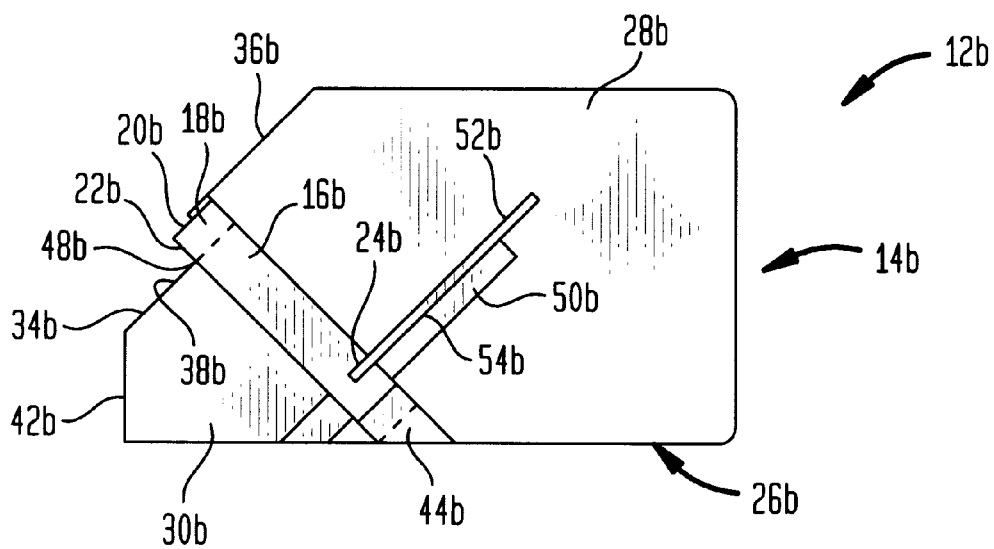
FIG. 5 is a top plane view of the other die shown in FIG. 3.

Referring to FIGS. 3 and 5, the die 12b, which has a construction similar to that of the die 12a, is provided with a base die member 14b and a sliding die member 16b which is movably mounted in the base die member 14b. More particularly, the sliding die member 16b, which is provided with a thin, elongated box-like shape, includes a swaging portion 18b at one end thereof. The swaging portion 18b has an engaging surface 20b which lies in a plane substantially normal to a longitudinal axis C (see FIG. 3) of the sliding die member 16b. A contact surface 22b is formed in the swaging portion 18b. The contact surface 22b is substantially normal to the engaging surface 20b. A slit 24b is formed at an opposite end of the sliding die member 16b for a purpose to be discussed hereinafter. The swaging portion 18b has a thickness (i.e., the distance measured in a direction substantially parallel to both of the planes associated with the engaging and contact surfaces 20b, 22b ) which is substantially identical to that of the swaging portion 18a and the tip portion 32a of the die 12a. As a result, the contact surface 22b has a height (i.e., a land width) substantially identical to those of the contact surfaces 22a, 38a of the die 12a.

Still referring to FIGS. 3 and 5, the base die member 14b includes a body 26b having a surface 28b which lies in a plane substantially parallel to a longitudinal axis D of the body 26b. The body 26b also has a projection 30b having a side 34b oriented substantially at a 45° angle with respect to the longitudinal axis D of the body 26b. The projection 30b also includes a contact surface 38b formed in the side 34b and lying in a plane which is oriented at a similar acute angle (e.g., a 45° angle) relative to the longitudinal axis D of the body 26b and which is substantially normal to the plane associated with the surface 28b of the body 26b. The projection 30b has a uniform thickness (i.e., the distance measured along a direction substantially normal to the surface 28b of the body 26b ) which is substantially identical to those of the swaging portion 18a and the tip portion 32a of the die 12a, as well as the swaging portion 18b of the die 12b As a result, the contact surface 38b has a height (i.e., a land width) substantially identical to those of the contact surfaces 22a, 22b, 38a. A shoulder 42b is formed on the projection 30b and therefore forms the leading end of the body 26b. More particularly, the shoulder 42b is oriented substantially perpendicular to the longitudinal axis D of the body 26b and is sized and shaped so as to engage the shoulder 42a of the die 12a. A side 36b is also formed on the body 26b. The side 36b is inclined at an acute angle relative to the longitudinal axis D of the body 26b.

With reference to FIGS. 3 and 5, the body 26b also includes a groove 44b formed in the surface 28b of the body 26b. The groove 44b extends from the contact surface 38b of the projection 30b to an opposite side of the body 26b along a direction substantially normal to the plane associated with the contact surface 38b. The groove 44b is sized and shaped so as to movably receive the sliding die member 16b. More particularly, the sliding die member 16b is placed in the groove 44b in such a manner that the contact surface 22b of the sliding die member 16b is oriented substantially normal to the contact surface 38b of the projection 30b. The groove 44b is also sized and shaped in such a manner that the sliding die member 16b is movable along a direction substantially normal to the plane associated with the contact surface 38b of the projection 30b between a fully extended position (as indicated by the solid line representation of the sliding die member 16b in FIG. 5) and a fully retracted position (as indicated by the broken line representation of the sliding die member 16b in FIG. 5). In the extended position of the sliding die member 16b, the swaging portion 18b of the sliding die member 16b projects outwardly from the groove 44b in dimension greater than an outer diameter of a surgical needle to be swaged. That is, the contact surface 22b of the sliding die member 16b extends outwardly from (i.e., beyond) the contact surface 38b of the projection 30b at a substantially right angle and thereby cooperates with same to form a V-shaped space 48b. In the retracted position of the sliding die member 16b, the swaging portion 18b is completely retracted into the groove 44b. In other words, the engaging surface 20b of the sliding die member 16b is substantially flush (i.e., coplanar) with the contact surface 38b of the projection 30b (i.e., the contact surface 22b of the sliding die member 16b does not extend beyond the contact surface 38b of the projection 30b ). The groove 44b also has a depth (measured in a direction substantially normal to the surface 28b of the body 26b ) such that the contact surface 22b of the sliding die member 16b is substantially aligned with the contact surface 38b of the projection 30b and that the sliding die member 16b does not protrude above the groove 44b.

Still referring to FIGS. 3 and 5, the body 26b has a channel 50b and a slot 52b formed in the surface 28b. More particularly, the channel 50b intersects the groove 44b, while the slot 52b extends from an end of the channel 50b away from the groove 44b. The body 26b is also provided with a leaf spring 54b positioned in the channel 50b for causing the sliding die member 16b to normally assume its extended position. More particularly, the leaf spring 54b has one end inserted in the slot 52b of the body 26b and an opposite end inserted in the slit 24b of the sliding die member 16b. The channel 50b is sized and shaped so as to allow the leaf spring 54b to resiliently bend in response to the movement of the sliding die member 16b. When the sliding die member 16b moves towards its retracted position, the leaf spring 54b urges the sliding die member 16b towards the extended position.

With reference to FIGS. 1–3, the die 12b is also provided with a holding plate 56b applied to the surface 28b of the body 26b of the base die member 14b in such a position that the holding plate 56b does not interfere with the engagement of the die 12b with the die 12a. The holding plate 56b is adapted to contain the sliding die member 16b and the leaf spring 54b in the groove 44b and the channel 50b, respectively, during operation.

Figure 8:
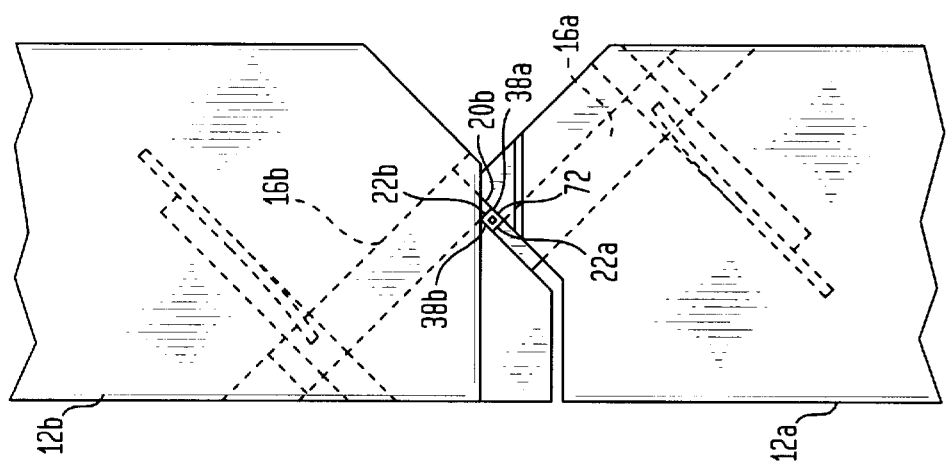
FIGS. 6–8 are schematic views illustrating the operation of the swaging apparatus shown in FIGS. 1–3.

A movable die holder 60b (see FIGS. 1 and 2) holds the die 12b in proper relation relative to the holding plate 56b, as well as to the die 12a. More particularly, the die 12b is positioned relative to the die 12a in such an orientation that the contact surfaces 22b, 38b of the die 12b are aligned with the contact surfaces 22a, 38a of the die 12a (see FIGS. 1, 2 and 6–8). The movable die holder 60b is movably mounted on the press (not shown). As a result, the die 12b is movable between its retracted position, in which it is out of engagement with the die 12a and thereby forms an open gap (i.e., space) 62 between the dies 12a, 12b (see FIGS. 1, 2 and 6), and its predetermined swaging (i.e., bottom) position, in which it engages the die 12a so as to cooperate with same to perform a swaging function (see FIG. 8), as will be discussed further hereinafter.

Figure 6:
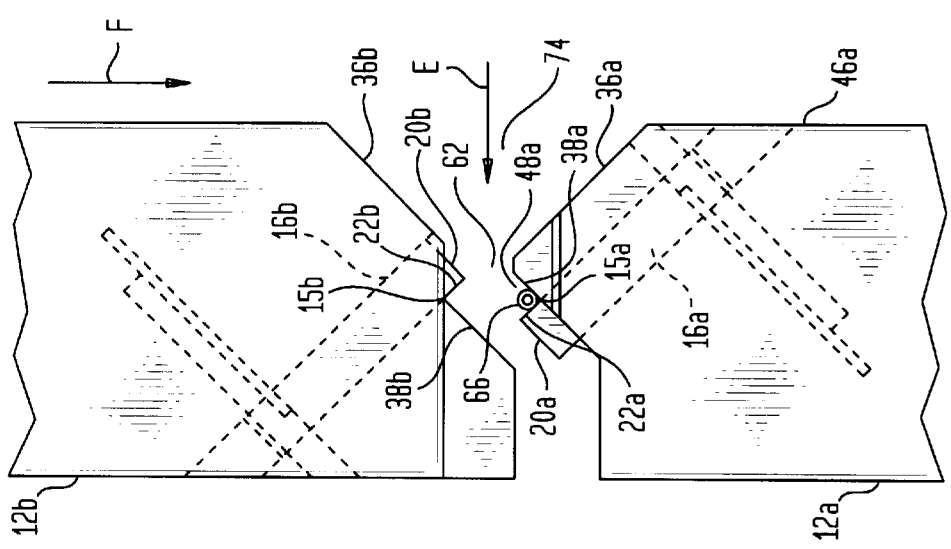
Figure 9:
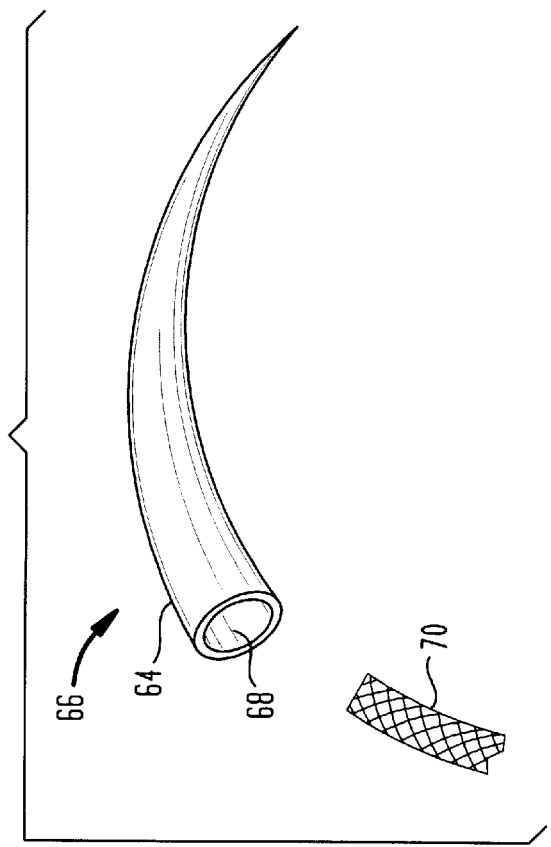
FIGS. 9 and 10 are views of a surgical needle before and after a swaging operation performed by the apparatus shown in FIGS. 1–8.

In operation, the die 12b is initially positioned in its retracted position (see FIG. 6). A mounting end 64 of a surgical needle 66 (see FIG. 9) is manually inserted in the V-shaped space 48a of the die 12a from the side 46a of the die 12a through the gap 62 (as indicated by the arrow E in FIG. 6). More particularly, the mounting end 64 of the needle 66 is properly placed in the V-shaped space 48a such that a hole 68 formed in the mounting end 64 of the needle 66 faces the notch 58a of the holding plate 56a (i.e., the hole 68 is aligned with the notch 58a ). Next, guided by the notch 58a of the holding plate 56a, an end of a suture 70 (see FIG. 9) is manually inserted into the hole 68 of the needle 66. In this regard, it should be noted that the position of the holding plate 56a is adjustable relative to the die 12a to sufficiently align the notch 58a to the hole 68 of the needle 66 for guiding the suture 70 into same. With the needle 66 and the suture 70 manually held in place, an operator activates the press, causing the movable die holder 60b and therefore the die 12b to move towards the die 12a. That is, the die 12b moves from its retracted position towards its predetermined swaging position along a direction substantially parallel to the longitudinal axis B of the die 12a and/or the longitudinal axis D of the die 12b (as indicated by the arrow F in FIG. 6).

Figure 7:
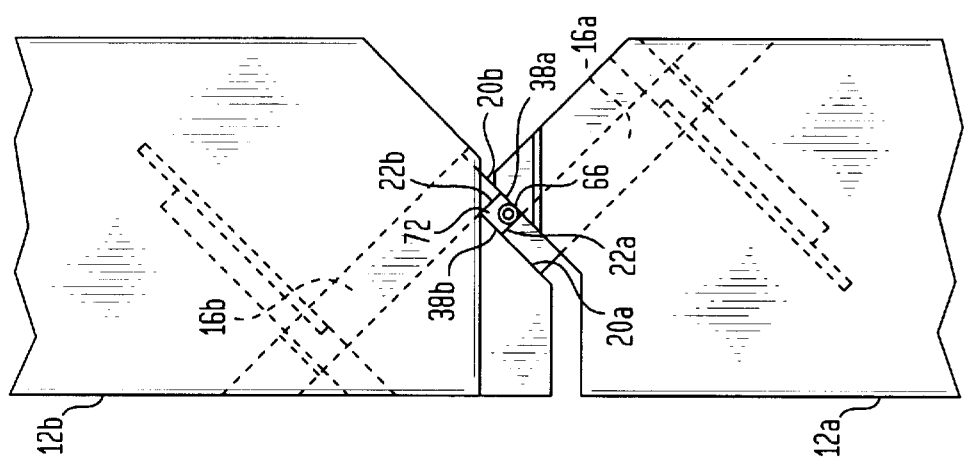

As the die 12b moves towards its predetermined swaging position, it comes to its intermediate position, in which the engaging surface 20b and the contact surface 38b of the die 12b come in contact with the contact surface 38a and the engaging surface 20a, respectively, of the die 12a (see FIG. 7). Preferably, the die 12b moves from its retracted position to its predetermined swaging position in one continuous stroke without stopping at its intermediate position. Alternatively, the die 12b can temporarily stop at its intermediate position so as to cooperate with the die 12a in loosely griping the mounting end 64 of the needle 66, thereby stabilizing the needle 66 for a swaging operation to be performed thereon.

In the intermediate position of the die 12b, the sliding die members 16a, 16b are substantially in their fully extended positions. Because the contact surfaces 22a, 22b project from the contact surfaces 38a, 38b, respectively, in dimension greater than the outer diameter of the mounting end 64 of the needle 66 (see FIG. 7), the contact surfaces 22a, 22b, 38a, 38b completely surround the entire circumference of the mounting end 64 of the needle 66 without compressing the mounting end 64. In other words, the contact surfaces 22a, 22b, 38a, 38b cooperate to form an enclosed swaging space 72 in which the mounting end 64 of the needle 66 is located.

Figure 10:
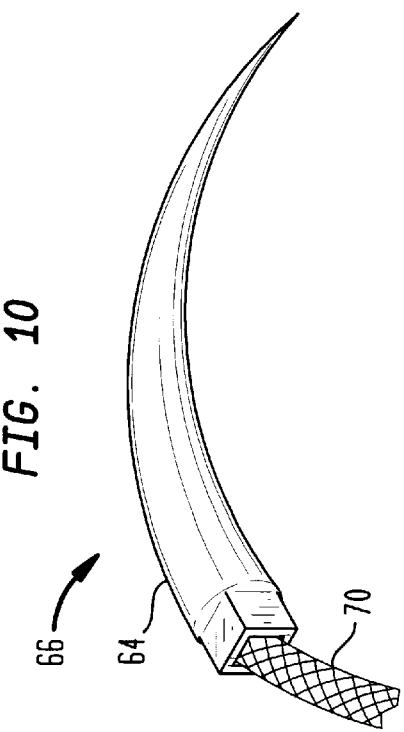

As the die 12b continues to move towards its predetermined swaging position, the engaging surfaces 20a, 20b of the sliding die members 16a, 16b, respectively, slide along the contact surfaces 38b, 38a, respectively, of the dies 12b, 12a, respectively, while the sliding die members 16a, 16b are biased by the contact surfaces 38b, 38a, respectively, of the dies 12b, 12a, respectively, so as to be moved towards their retracted positions. More particularly, the contact surfaces 22a, 22b, 38a, 38b converge with one another (i.e., the contact surface 22b and the contact surface 38b simultaneously converge towards the contact surface 22a and the contact surface 38a, respectively). As a result, the enclosed space 72 is progressively and symmetrically decreased in dimension. In this manner, the contact surfaces 22a, 22b, 38a, 38b cooperate with one another to progressively and simultaneously compress the outer surface of the mounting end 64 of the needle 66 into a predetermined shape (i.e., a square cross-sectional shape) and a predetermined size, thereby securely attaching the suture 70 to the mounting end 64 of the needle 66 (see FIGS. 8 and 10).

Upon reaching its predetermined swaging position, the die 12b returns to its retracted position, thereby releasing the swaged mounting end 64 of the needle 66. The needle 66 and the attached suture 70 is then removed from the die 12a and/or die 12b through the gap 62 formed between the dies 12a, 12b. The suture and needle combination may then be manually or automatically pull-tested in a conventional manner to determine whether the suture 70 is properly secured to the needle 66.

It should be appreciated that the swaging apparatus 10 of the present invention provides numerous advantages over the conventional swaging devices discussed above. For instance, because the contact surfaces 22a, 22b, 38a, 38b are adapted to converge one another to any predetermined extent, the dies 12a, 12b can swage an associated surgical needle to any preselected extent or size. More particularly, the die 12b is adapted to be displaced to any position between its intermediate position, in which the contact surfaces 22a, 22b, 38a, 38b are diverged from one another (see FIG. 7), and its fully extended position, in which the contact surfaces 22a, 22b, 38a, 38b are completely converged with one another and thereby close off the enclosed space 72. That is, in its fully extended position, the die 12b abuts the die 12a and thereby causes the sliding die members 16a, 16b to be moved to their fully retracted positions. As a result, by simply adjusting the displacement (i.e., the stroke length) of the die 12b relative the die 12a, the dies 12a, 12b are adapted to compress an associated surgical needle to any desired extent. In other words, the extent to which the dies 12a, 12b swage an associated surgical needle is infinitely adjustable.

Owning to their infinite adjustability, the dies 12a, 12b are adapted for "universal" use in connection with any sizes and/or types of needles and sutures, thereby eliminating the need to provide numerous die sets required by the prior art. For instance, the dies 12a, 12b are adapted for "universally" swaging surgical needles having different outer diameters and/or hole sizes by adjusting the predetermined swaging position of the die 12b relative to die 12a. Further, by using the swaging apparatus 10, a surgical needle having a predetermined hole size can be attached to any one of many varying sizes and types of sutures.

It should be noted that there are numerous ways of adjusting and/or controlling the displacement (i.e., the stroke length) of the die 12b relative to die 12a. For instance, the predetermined swaging (i.e., bottom) position of the die 12b can be fine-tuned by controlling a fine-tune adjustment screw 75 (see FIG. 2) associated with the die holder 60b. Greater adjustments can be made by adjusting the vertical position of the die 12b relative to the die holder 60b. In addition, the associated press can be adjusted in a conventional manner to control the displacement or the stroke length of an associated piston or piston-like mechanism, thereby controlling the stroke length of the die 12b.

It should also be appreciated that because the contact surfaces 22a, 22b, 38a, 38b completely surround a mounting end of an associated surgical needle throughout a swaging operation, the swaging apparatus 10 is adapted to properly swage the needle substantially without defects. More particularly, because the engaging surfaces 20a, 20b of the sliding die member 16a, 16b, respectively, are urged against the contact surfaces, 38b, 38a, respectively, throughout a swaging operation, the needle is inhibited from forming fins (i.e., defects formed by the material of the needle flowing outwardly through spaces formed between conventional dies).

In addition to the advantages mentioned above, there are other advantages that are noteworthy herein. For instance, because the extent to which the contact surfaces 22a, 22b, 38a, 38b converge with one another can be easily adjusted, wear and tear of the contact surfaces 22a, 22b, 38a, 38b can be compensated. Moreover, the sides 36a, 36b of the dies 12a 12b, respectively facilitate insertion and removal of a surgical needle. More particularly, because the sides 36a, 36b diverge from each other, they form a clearance 74 (see FIG. 6) through which a surgical needle can be inserted and removed. Moreover, the shoulders 42a, 42b of the dies 12a, 12b, respectively, are adapted to come in contact and cooperate with each other to inhibit the die 12b from moving beyond its fully extended position. In other words, the shoulders 42a, 42b function as a stop mechanism for the dies 12a, 12b, thereby inhibiting inadvertent damages to the contact surfaces 22a, 22b, 38a, 38b.

It should be noted that the swaging apparatus 10 can have numerous modifications and variations. For instance, the holding plate 56a and/or the holding plate 56b can be eliminated or replaced with other mechanisms. Moreover, each of the contact surfaces 22a, 22b, 38a, 38b can have different thicknesses or widths. The contact surfaces 22a, 22b, 38a, 38b can also be provided with inserts which can be replaced upon wear and tear. Further, while the dies 12a, 12b and the contact surfaces 22a, 22b, 38a, 38b are preferably made from high speed tool steel and carbide, respectively, they can be made from other conventional materials. Moreover, while a single set of dies constructed in accordance with the present invention can be used for all types and sizes of surgical needles and/or sutures, it might be preferable, in certain situations, to provide a few sets of dies, each of such sets having a different contact surface width and thereby a different land width. In addition, the leaf springs 54a, 54b can be replaced with other urging mechanisms, such as coil springs.

The dies 12a, 12b can also be modified to swage an associated surgical needle into a number of different geometrical cross-sectional shapes. For instance, each of the contact surfaces 22a, 38a of the die 12a and the contact surfaces 22b, 38b of the die 12b can be provided with a tip having a round surface so as to form a round (i.e., circular) cross-sectional shape.

Moreover, the contact surfaces 38a, 38b can be oriented at angles other than 90° with respect to the contact surfaces 22a, 22b, respectively, to form a parallelogram, triangular or trapezoidal crosssectional shape.

Different cross-sectional shapes for swaged needles can also be obtained by changing the direction of movement of the die 12b relative to the die 12a. More particularly, in the swaging apparatus 10, the die 12b moves in a direction which is substantially at a 45° angle relative to the contact surfaces 22a, 22b, 38a, 38b. In other words, a corner 15b defined by the contact surfaces 22b, 38b (see FIG. 6) moves towards a corner 15a defined by the contact surfaces 22a, 38a (see FIG. 6) along the same 45° angle direction. By changing the direction (i.e., the angle) in which the corner 15b of the die 12b approaches the corner 15a of the die 12a with respect to the contact surfaces 22a, 22b, 38a, 38b, different rectangular cross-sectional shapes can be obtained.

The manner of operating the swaging apparatus 10 can also have numerous modifications and variations. For instance, an associated suture can be inserted into the hole of a needle when the needle is partially gripped between the dies 12a, 12b (i.e., when the die 12b is in its intermediate position). In this manner, the insertion of the suture into the hole is facilitated. Moreover, a suture can be inserted into a needle before the needle is placed in the V-Shaped space 48a. In addition, the entire swaging process can be automated in a conventional manner so as to enhance the efficiency of the swaging apparatus 10. More particularly, in automated operation, a surgical needle 66 is automatically placed at a predetermined common center location positioned between the dies 12a, 12b. Both of the dies 12a, 12b then move towards the center location. That is, the corner 15a of the die 12a (see FIG. 6) and the corner 15b of the die 12a (see FIG. 6) converge towards the center location, thereby swaging the mounting end of the surgical needle 66 in the manner described above. Next, the dies 12a, 12b move away from the center location, allowing the swaged surgical needle 66 to be automatically removed and pull-tested. In an automated swaging system, a feedback mechanism can be used for automatically adjusting the stoke length of the die 12a and/or the die 12b after a pull-test.

FIGS. 11–20 show various alternate embodiments of the present invention. Elements illustrated in FIGS. 11 and 12, FIGS. 13 and 14, FIGS. 15 and 16, FIGS. 17 and 18 and FIGS. 19 and 20, which correspond, either identically or substantially, to the elements described above with respect to the embodiment of FIGS. 1–10, have been designated by corresponding reference numerals increased by one hundred, two hundred, three hundred, four hundred and five hundred, respectively. Unless otherwise stated, the embodiments of FIGS. 11–20 are constructed, assembled and operated in the same basic manner as the embodiment of FIGS. 1–10.

Figure 11:
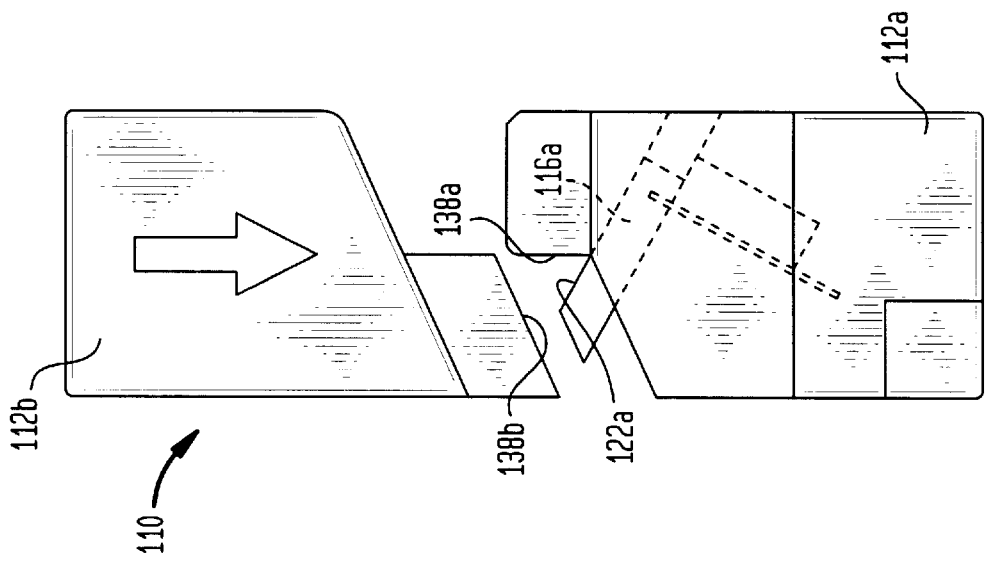
FIG. 11 is a schematic view of a swaging apparatus constructed in accordance with a second embodiment of the present invention.

FIG. 11 shows a swaging apparatus 110 having a pair of swaging dies 112a, 112b. The die 112a includes a contact surface 138a and a sliding die 116a having a contact surface 122a, while the die 112b includes a contact surface 138b. The contact surfaces 122a, 138a, 138b are sized, shaped, oriented and arranged relative to each other in such a way that they cooperate with one another to swage a mounting end 164 of a surgical needle 166 into a triangular cross-sectional shape (see FIG. 12) when the swaging die 112b moves from its retracted position to its predetermined swaging position.

FIG. 13 shows a swaging apparatus 210 having a pair of swaging dies 212a, 212b.

The die 212a includes a contact surface 238a and a pair of sliding die members 216a, each of which has a contact surface 222a. Likewise, the die 212b includes a contact surface 238b and a sliding die member 216b having a contact surface 222b. The contact surfaces 222a, 222b, 238a, 238b are sized, shaped, oriented and arranged relative to each other in such a way that they cooperate with one another to swage a mounting end 264 of a surgical needle 266 into a pentagonal cross-sectional shape (see FIG. 14) when the die 212b moves to its predetermined swaging position from its retracted position.

Figure 15:
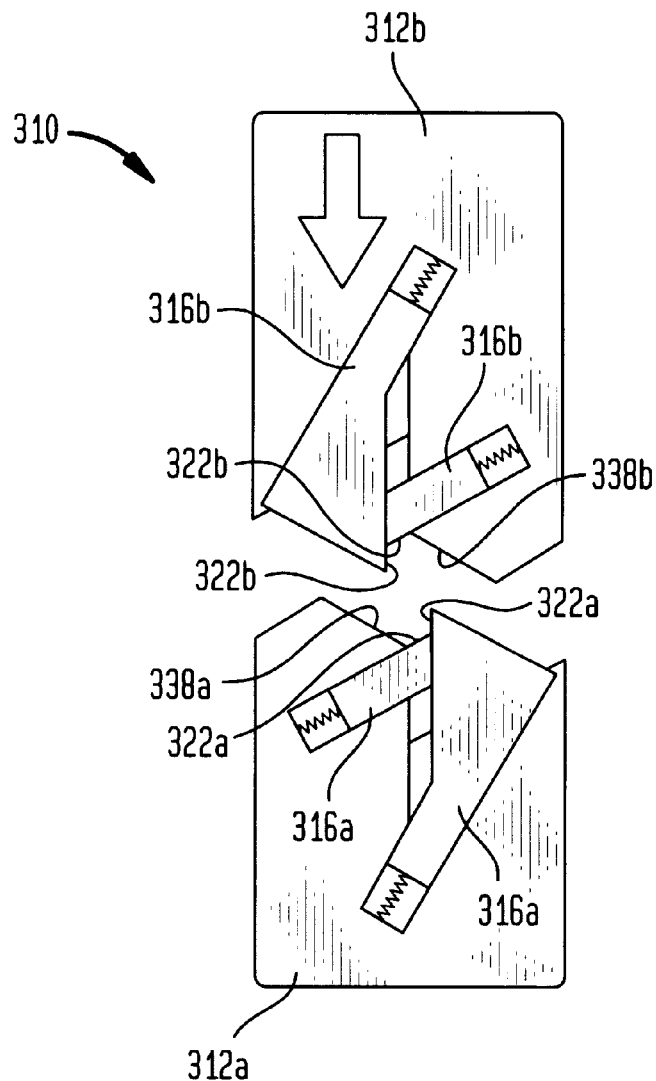
FIG. 15 is a schematic view of a swaging apparatus constructed in accordance with a fourth embodiment of the present invention.
Figure 16:
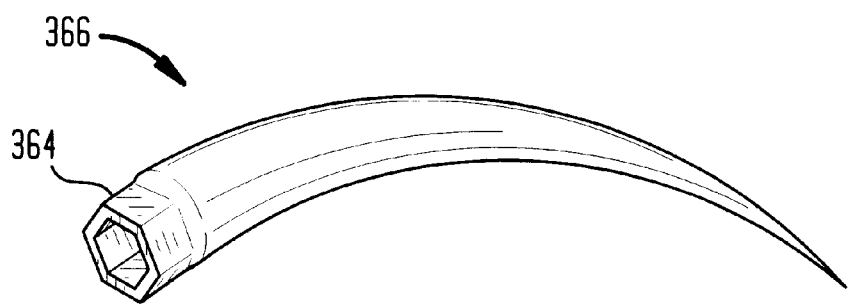
FIG. 16 is a view of a surgical needle swaged by the apparatus shown in FIG. 15.

FIG. 15 shows a swaging apparatus 310 having a pair of swaging dies 312a, 312b. The die 312a includes a contact surface 338a and a pair of sliding die members 316a, each of which has a contact surface 322a. Likewise, the die 312b includes a contact surface 338b and a pair of sliding die members 316b, each of which has a contact surface 322b. The contact surfaces 322a, 322b, 338a, 338b are sized, shaped, oriented and arranged relative to each other in such a way that they cooperate with one another to swage a mounting end 364 of a surgical needle 366 into a hexagonal cross-sectional shape (see FIG. 16) when the die 312b moves to its predetermined swaging position from its retracted position.

Figure 17:
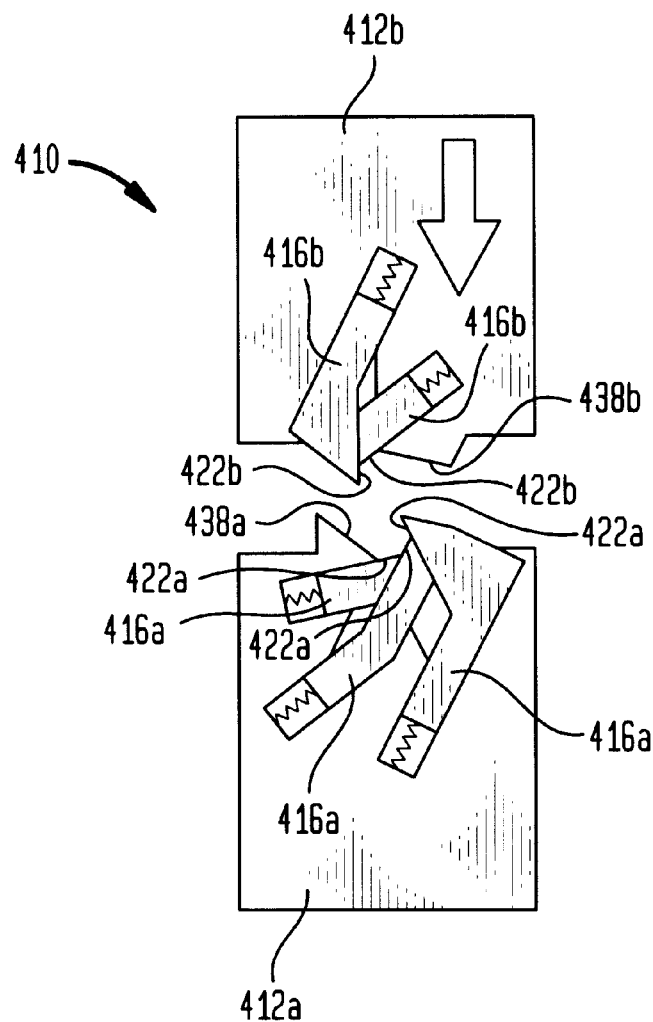
FIG. 17 is a schematic view of a swaging apparatus constructed in accordance with a fifth embodiment of the present invention.
Figure 18:
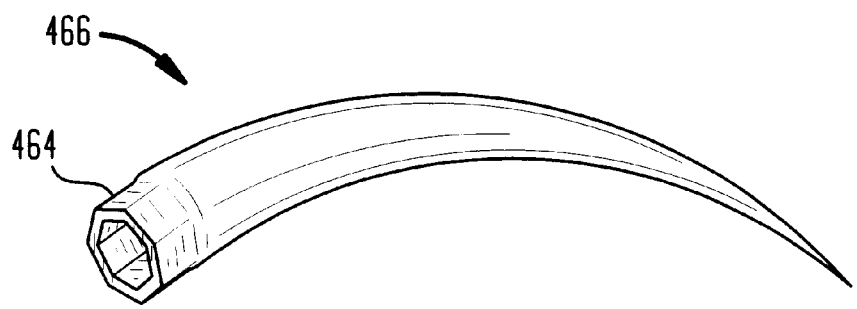
FIG. 18 is a view of a surgical needle swaged by the apparatus shown in FIG. 17.

FIG. 17 shows a swaging apparatus 410 having a pair of swaging dies 412a, 412b.

The die 412a includes a contact surface 438a and three sliding die members 416a, each of which has a contact surface 422a. Likewise, the die 412b includes a contact surface 438b and a pair of sliding die members 416b, each of which has a contact surface 422b. The contact surfaces 422a, 422b, 438a, 438b are sized, shaped, oriented and arranged relative to each other in such a way that they cooperate with one another to swage a mounting end 464 of a surgical needle 466 into a heptagonal cross-sectional shape (see FIG. 18) when the die 412b moves to its predetermined swaging position from its retracted position.

Figure 19:
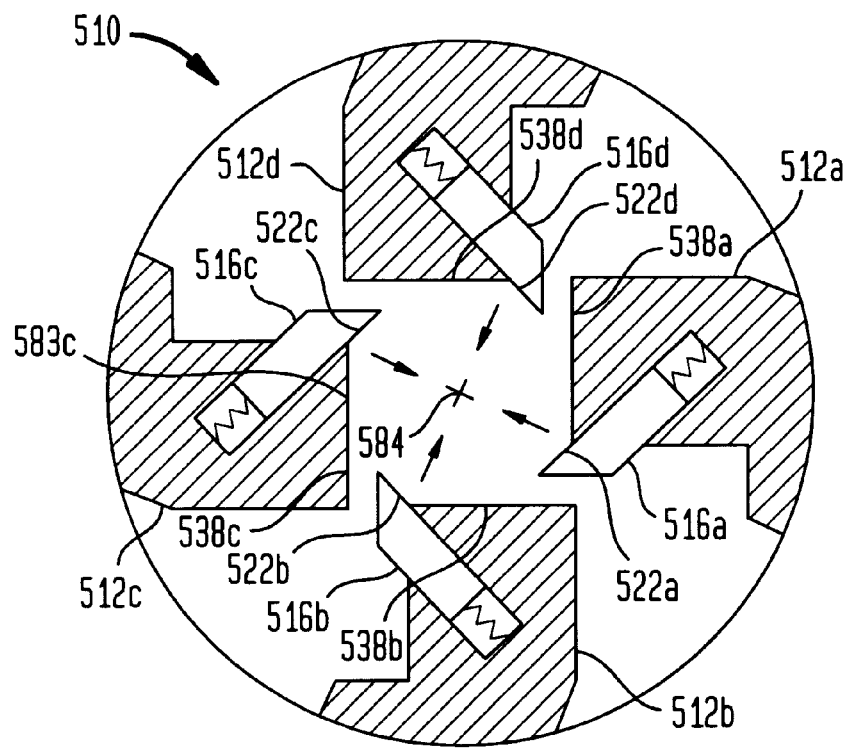
FIG. 19 is a schematic view of a swaging apparatus constructed in accordance with a sixth embodiment of invention.
Figure 20:
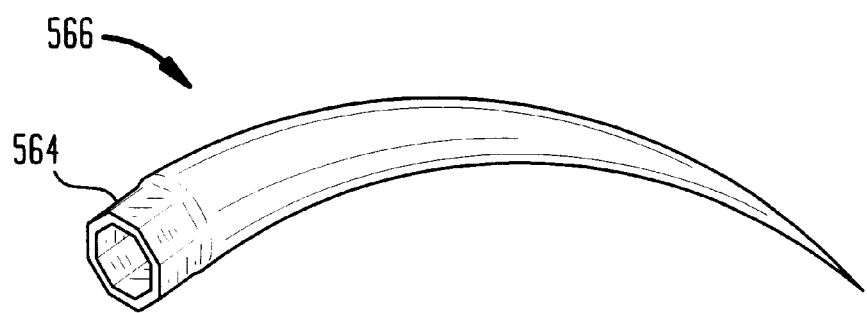
FIG. 20 is a view of a surgical needle swaged by the apparatus shown in FIG. 19.

FIG. 19 shows a swaging apparatus 510 having four swaging dies 512a, 512b, 512c, 512d. The dies 512a –512d include contact surfaces 538a, 538b, 538c, 538d, respectively, and sliding die members 516a, 516b, 516c, 516d, respectively, which have contact surfaces 522a, 522b, 522c, 522d, respectively. The dies 512a –512d are adapted to converge each other (as indicated by the arrows in FIG. 19). That is, each of the dies 512a –512d is movable towards a common center 584. The contact surfaces 522a –522d, 538a –538d are sized, shaped, oriented and arranged relative to each other in such a way that they cooperate with one another to swage a mounting end 564 of a surgical needle 566 into an octagonal cross-sectional shape (see FIG. 20) when the dies 512a 512d move to their predetermined swaging positions.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

We claim:

1. Apparatus for swaging a surgical needle to attach a suture thereto, comprising a first die having a first member, which includes a first surface, and a second member, which includes a second surface, said second member being movable relative to said first member between an extended position, in which said second surface projects beyond said first surface, and a retracted position, in which said second surface does not project beyond said first surface, said first die including urging means for urging said second member towards its said extended position; and at least one other die including at least one surface, said at least one other die being movable relative to said first die between a first position, in which said at least one other die is remote from said first die, and a second position, in which said at least one other die is positioned adjacent to said first die, said at least one other die causing said second member of said first die to move from its said extended position towards its said retracted position when said at least one other die moves relative to said first die from its said first position towards its said second position, said at least one surface of said at least one other die cooperating with said first and second surfaces of said first die so as to swage a surgical needle positioned between said first die and said at least one other die when said at least one other die moves relative to said first die from its said first position towards its said second position, and said second member of said first die being movable to its said retracted position when said at least one other die abuts said first die, whereby surgical needles of many different types or sizes can be swaged by said first die and said at least one other die.

2. The apparatus of claim 1, wherein said first and second surfaces of said first die and said at least one surface of said at least one other die cooperate with one another so as to define a space therebetween and to thereby position a mounting end of a surgical needle to be swaged in said space when said at least one other die moves relative to said first die from its said first position towards its said second position.

3. The apparatus of claim 2, wherein said first and second surfaces of said first die and said at least one surface of said at least one other die cooperate with one another so as to progressively decrease the size of said space when said at least one other die moves relative to said first die from its said first position towards its said second position, whereby said first and second surfaces of said first die and said at least one surface of said at least one other die progressively swage a mounting end of a surgical needle positioned in said space.

4. The apparatus of claim 3, wherein said at least one other die is movable relative to said first die to one of an infinite number of positions between its said first position and its said second position such that said first die and said at least one other die can swage a surgical needle positioned in said space to an infinitely variable extent.

5. The apparatus of claim 4, wherein said at least one other die includes a second die having a third member and a fourth member, said at least one surface including a third surface, which is formed on said third member, and a fourth surface, which is formed on said fourth member, said fourth member of said second die being movable relative to said third member of said second die between an extended position, in which said fourth surface projects beyond said third surface, and a retracted position, in which said fourth surface does not project beyond said third surface, said second die including another urging means for urging said fourth member towards its said extended position.

6. The apparatus of claim 5, wherein said third and fourth surfaces of said second die simultaneously move towards said first and second surfaces, respectively, of said first die when said second die moves relative to said first die from said first position towards said second position.

7. The apparatus of claim 6, wherein said second member of said first die includes a fifth surface at an end thereof, said fifth surface being substantially coplanar with said first surface when said second member is in its said retracted position; and wherein said fourth member of said second die includes a sixth surface at an end thereof, said sixth surface being substantially coplanar with said third surface when said fourth member is in its said retracted position.

8. The apparatus of claim 7, wherein said first and second surfaces of said first die cooperate with said third and fourth surfaces so as to completely surround a mounting end of a surgical needle prior to the performance of a swaging operation by said first and second dies.

9. The apparatus of claim 5, wherein said first die includes a fifth member which is movable relative to said first member of said first die between an extended position and a retracted position in response to the movement of said second die relative to said first die, said at least one surface including a fifth surface formed on said fifth member, said first, second, third, fourth and fifth surfaces cooperating with one another so as to swage a mounting end of a surgical needle positioned between said first and second dies when said second die moves relative to said first die from said first position towards said second position.

10. The apparatus of claim 9, wherein said second die includes a sixth member movable relative to said third member of said second die between an extended position and a retracted position in response to the movement of said second die relative to said first die, said at least one surface including a sixth surface formed on said sixth member, said first, second, third, fourth, fifth and sixth surfaces cooperating with one another so as to swage a mounting end of a surgical needle positioned between said first and second dies when said second die moves relative to said first die from said first position towards said second position.

11. The apparatus of claim 10, wherein said first die includes a seventh member, which is movable relative to said first member of said first die between an extended position and a retracted position in response to the movement of said second die relative to said first die, said at least one surface including a seventh surface formed on said seventh member, said first, second, third, fourth, fifth, sixth and seventh surfaces cooperating with one another so as to swage a mounting end of a surgical needle positioned between said first and second dies when said second die moves relative to said first die from said first position towards said second position.

12. The apparatus of claim 5, wherein said at least one other die includes a third die, which has a fifth member and a sixth member, and a fourth die, which has a seventh member and an eighth member, said at least one surface including a fifth surface, which is formed on said fifth member of said third die, a sixth surface, which is formed on said sixth member of said third die, a seventh surface, which is formed on said seventh member of said fourth die, and an eighth surface, which is formed on said eighth member of said fourth die, said sixth member of said third die being movable relative to said fifth member of said third die between an extended position, in which said sixth surface extends beyond said fifth surface, and a retracted position, in which said sixth surface does not extend beyond said fifth surface, said eighth member of said fourth die being movable relative said seventh member of said fourth die between an extended position, in which said eighth surface extends beyond said seventh surface, and a retracted position, in which said eighth surface does not extend beyond said seventh surface, each of said first, second, third and fourth dies being movable towards and away from a common center, said second, fourth, sixth and eighth members moving towards their retracted positions in response to the movement of said first, second, third and fourth dies towards said common center, and said first, second, third, fourth, fifth, sixth, seventh and eighth surfaces cooperating with one another so as to swage a mounting end of a surgical needle positioned between said first, second, third and fourth dies when said first, second, third and fourth dies move towards said common center.

13. The apparatus of claim 5, wherein said second die is movable relative to said first die in such a direction that said first, second, third and fourth surfaces cooperate with one another so as to swage a mounting end of a surgical needle positioned between said first and second dies into a square cross-sectional shape.

14. The apparatus of claim 1, further comprising guiding means for guiding a suture into a mounting end of a surgical needle positioned between said first die and said at least one other die.

15. The apparatus of claim 1, wherein said first die includes mounting means for movably mounting said second member of said first die in said first member of said first die.

16. The apparatus of claim 15, wherein said mounting means includes a groove formed in said first die, said second member of said first die being positioned in said groove, said groove being sized and shaped so as to allow said second member of said first die to move between its said extended position and its said retracted position.

17. The apparatus of claim 16, wherein said groove is formed in said first member of said first die and extends from said first surface of said first member towards a remote side of said first member; and wherein said second member includes a portion which projects outwardly from said groove and hence said first surface of said first member when said second member is in its said extended position and which is retracted into said groove when said second member is in its said retracted position.

18. The apparatus of claim 17, wherein said first member includes a channel therein, said channel intersecting said groove; and wherein said urging means includes a leaf spring positioned in said channel and having one end, which is secured to said first member of said first die, and an opposite end, which is secured to said second member of said first die.

19. Apparatus for swaging a surgical needle to attach a suture thereto, comprising a first die having a first member, which includes a first surface, and a second member, which includes a second surface, said second member being movable relative to said first member between an extended position, in which said second surface projects beyond said first surface, and a retracted position, in which said second surface does not project beyond said first surface, said first die including first urging means for urging said second member towards its said extended position; and a second die having a third member, which includes a third surface, and a fourth member, which includes a fourth surface, said fourth member of said second die being movable relative to said third member of said second die between an extended position, in which said fourth surface projects beyond said third surface, and a retracted position, in which said fourth surface does not project beyond said third surface, said second die including second urging means for urging said fourth member towards its said extended position, said second die being movable relative to said first die between a first position, in which said second die is remote from said first die, and a second position, in which said second die is positioned adjacent to said first die, said second die causing said second member of said first die to move from its said extended position towards its said retracted position when said second die moves relative to said first die from its said first position towards its said second position, said first die causing said fourth member of second die to move from its said extended position towards its said retracted position when said second die moves relative to said first die from its said first position towards its said second position, said third and fourth surfaces of said second die cooperating with said first and second surfaces of said first die so as to swage a surgical needle positioned between said first die and said second die when said second die moves relative to said first die from its said first position towards its said second position, said second member of said first die and said fourth member of said second die being movable to their said retracted positions when said second die abuts said first die, whereby surgical needles of many different types or sizes can be swaged by said first die and said second die, said first and second surfaces of said first die and said third and fourth surfaces of said second die cooperating with one another to define a space for capturing a mounting end of a surgical needle and to progressively decrease the size of said space when said second die moves relative to said first die from its said first position towards its said second position, whereby said first and second surfaces of said first die and said third and fourth surfaces of said second die progressively swage a mounting end of a surgical needle positioned in said space, said second die being movable relative to said first die to one of an infinite number of positions between its said first position and its said second position such that said first die and said second die can swage a surgical needle positioned in said space to an infinitely variable extent, said third and fourth surfaces of said second die being simultaneously movable towards said first and second surfaces, respectively, of said first die when said second die moves relative to said first die from its said first position towards its said second position, and said space being completely closable when said second and fourth members of said first and second dies, respectively, are urged to their said retracted positions by said third surface of said second die and said first surface of said first die, respectively.

20. Apparatus for swaging a surgical needle to attach a suture thereto, comprising a first die having a first member, which includes a first surface, and a second member, which includes a second surface, said second member being movable relative to said first member between an extended position, in which said second surface projects beyond said first surface, and a retracted position, in which said second surface does not project beyond said first surface, said first die including first urging means for urging said second member towards its said extended position; and a second die having a third member, which includes a third surface, and a fourth member, which includes a fourth surface, said fourth member of said second die being movable relative to said third member of said second die between an extended position, in which said fourth surface projects beyond said third surface, and a retracted position, in which said fourth surface does not project beyond said third surface, said second die including second urging means for urging said fourth member towards its said extended position, said second die being movable relative to said first die between a first position, in which said second die is remote from said first die, and a second position, in which said second die is positioned adjacent to said first die, said second die and said first die causing said second member of said first die and said fourth member of said second die, respectively, to move from their said extended positions towards their said retracted positions when said second die moves relative to said first die from its said first position towards its said second position, said third and fourth surfaces of said second die cooperating with said first and second surfaces of said first die so as to swage a surgical needle positioned between said first die and said second die when said second die moves relative to said first die from its said first position towards its said second position, and said second member of said first die and said fourth member of said second die being movable to their said retracted positions when said second die abuts said first die, whereby surgical needles of many different types or sizes can be swaged by said first die and said second die.

21. The apparatus of claim 20, wherein said first, second, third and fourth surfaces have first, second, third and fourth widths, respectively, which are substantially identical to one another, whereby a surgical needle swaged by said first, second, third and fourth surfaces has a substantially uniform land width.

22. The apparatus of claim 21, wherein said second die member is positioned in its said retracted position when said second die abuts said first die; and wherein said fourth die member is positioned in its said retracted position when said second die abuts said first die.

23. The apparatus of claim 22, wherein said first, second, third and fourth surfaces cooperate to define a space for capturing a mounting end of a surgical needle, said space being closed off by said first, second, third and fourth surfaces when said second die is in its said second position.

* * * * *